United States Patent

Beauquey et al.

[11] Patent Number: 6,051,213
[45] Date of Patent: *Apr. 18, 2000

[54] DETERGENT COSMETIC COMPOSITIONS FOR HAIR USE AND USE THEREOF

[75] Inventors: Bernard Beauquey, Clichy; Daniele Cauwet, Paris; Sandrine Decoster, Epinay sur Seine; Claude Dubief, Le Chesnay, all of France

[73] Assignee: L'Oreal, Paris, France

[ * ] Notice: This patent is subject to a terminal disclaimer.

[21] Appl. No.: 09/044,129

[22] Filed: Mar. 19, 1998

Related U.S. Application Data

[63] Continuation of application No. 08/695,669, Aug. 8, 1996, Pat. No. 5,858,341, which is a continuation of application No. 08/362,849, Dec. 22, 1994, abandoned.

[30] Foreign Application Priority Data

Jan. 11, 1994 [FR] France .................................. 9400219

[51] Int. Cl.[7] .............................. A61K 7/07; A61K 7/075
[52] U.S. Cl. ................. 424/70.19; 424/70.1; 424/70.11; 514/557
[58] Field of Search .................... 424/70.1, 70.11–70.17, 424/401; 514/557

[56] References Cited

U.S. PATENT DOCUMENTS

| | | | |
|---|---|---|---|
| 1,811,809 | 6/1931 | Schwarzkopf | 424/70.1 |
| 3,322,676 | 5/1967 | Hiestand et al. | 252/152 |
| 3,836,537 | 9/1974 | Boerwinkle et al. | 260/29.6 |
| 3,996,146 | 12/1976 | Tarasov et al. | 252/142 |
| 4,217,914 | 8/1980 | Jacquet et al. | 132/7 |
| 4,445,521 | 5/1984 | Grollier et al. | 132/7 |
| 4,705,681 | 11/1987 | Maes et al. | 424/70.1 |
| 4,839,166 | 6/1989 | Grollier et al. | 424/71 |
| 4,996,059 | 2/1991 | Grollier et al. | 424/71 |
| 5,009,813 | 4/1991 | Watanabe et al. | 252/545 |
| 5,089,252 | 2/1992 | Grollier et al. | 424/71 |
| 5,091,171 | 2/1992 | Yu et al. | 424/62 |
| 5,858,341 | 1/1999 | Beaquey et al. | 424/70.19 |

FOREIGN PATENT DOCUMENTS

| | | |
|---|---|---|
| 0269243 | 6/1988 | European Pat. Off. . |
| 0337354 | 10/1989 | European Pat. Off. . |
| 0398177 | 11/1990 | European Pat. Off. . |
| 0403304 | 12/1990 | European Pat. Off. . |
| 0413528 | 2/1991 | European Pat. Off. . |
| 0 437 114 A1 | 7/1991 | European Pat. Off. . |
| 0492657 | 7/1992 | European Pat. Off. . |
| 0508324 | 10/1992 | European Pat. Off. . |
| 0531943 | 3/1993 | European Pat. Off. . |
| 2091516 | 1/1972 | France . |
| 2270846 | 1/1976 | France . |
| 2383660 | 10/1978 | France . |
| 2470596 | 6/1981 | France . |
| 2519863 | 7/1983 | France . |
| 2598611 | 11/1987 | France . |
| 2-218797 | 8/1990 | Japan . |
| 3-34914 | 2/1991 | Japan . |
| 93/15711 | 8/1993 | WIPO . |

OTHER PUBLICATIONS

Derwent Abstract of French Pat. App. 2,091,516, Jan. 14, 1972.

Flick, Ernest W., Cosmetic and Toiletry Formulations, vol. 2 (1992), pp. 644–645.

*Primary Examiner*—Jyothsna Venkat
*Attorney, Agent, or Firm*—Finnegan, Henderson, Farabow, Garrett & Dunner, L.L.P.

[57] ABSTRACT

Novel detergent hair compositions (shampoos) which are more particularly suitable for so-called sensitized hair, comprising a cosmetically acceptable medium containing at least one anionic surface-active agent, at least one nonionic surface-active agent, at least one conditioning agent, and at least 2% by weight relative to the total weight of the detergent hair composition of at least one carboxylic acid having a hydroxyl radical in the a position (alpha-hydroxy acid) or a derivative thereof.

The compositions make it possible to obtain hair which, after washing, has enhanced lightness, smoothness, shine and mechanical strength.

13 Claims, No Drawings

DETERGENT COSMETIC COMPOSITIONS FOR HAIR USE AND USE THEREOF

This is a continuation of application Ser. No. 08/695,669, filed Aug. 8, 1996 now U.S. Pat. No. 5,858,341, which is a continuation of Ser. No. 08/362,849, filed Dec. 22, 1994, now abandoned, which is incorporated herein by reference.

The present invention relates to novel cosmetic compositions, having enhanced properties, intended for the cleaning or care of the hair and/or the scalp, based on anionic surfactants, nonionic surfactants, conditioning agents and α-hydroxylated carboxylic acids or their derivatives, as well as the use of these novel compositions in this cosmetic application.

For the cleaning and/or care of the hair, it is common to use detergent hair compositions, or shampoos, containing both anionic surface-active agents and nonionic surface-active agents (mixtures). Indeed, it is known that these compositions possess excellent washing power, but the intrinsic cosmetic properties associated with them still remain relatively low.

Therefore, in order to enhance the cosmetic properties of the above detergent compositions and more particularly of those which are destined for application to sensitized hair, i.e., hair which is damaged or rendered fragile in particular under the chemical action of atmospheric agents and/or of hair treatments such as permanent waves, dyeing or bleaching, it is known to introduce into these compositions complementary cosmetic agents known as conditioning agents, in particular polymers, for example, such as cationic polymers, amphoteric polymers or, alternatively, silicones and/or silicone derivatives, which then provide the treated hair with a markedly improved facility for untangling and styling and markedly improved softness.

However, for such detergent compositions based on anionic and nonionic surfactants and conditioning agents, it is observed, in a manner which cannot be explained, that the cosmetic advantages mentioned above are unfortunately also accompanied, on dried hair, by certain cosmetic effects deemed to be undesirable, namely lankness of the hairstyle (lack of lightness of the hair), lack of smoothness (non-homogeneous hair from the root to the tip) and insufficient shine. Moreover, it is observed that these drawbacks are greatly accentuated in the case of application of the detergent composition to sensitized hair; in addition, if the hair has been sensitized by dyeing treatments, in particular by oxidation dyes, the repeated use of the detergent composition induces in the long run a harmful decrease in the mechanical strength of the hair.

In summary, the current detergent compositions containing anionic surfactants, nonionic surfactants and conditioning agents do not give complete satisfaction.

After considerable research conducted in this matter, it has been found by the inventors that by introducing, in a sufficient amount, α-hydroxylated carboxylic acids or their derivatives into the detergent hair compositions of the prior art based on anionic surfactants, nonionic surfactants and conditioning agents, it is possible to limit, or even to eliminate altogether, the problems generally associated with the use of such compositions, namely the lankness, the lack of smoothness and shine, and the lessening in mechanical strength of the hair, while at the same time conserving the washing power and the other advantageous cosmetic properties (softness, untangling, styling) which are associated with these compositions. This discovery forms the basis of the present invention.

Thus, according to the present invention, there are now proposed novel detergent hair compositions of the type comprising, in a cosmetically acceptable medium, at least one anionic surface-active agent, at least one nonionic surface-active agent and at least one conditioning agent, and these compositions additionally comprise, in an amount of at least 2% by weight relative to the whole of the composition, at least one carboxylic acid having a hydroxyl radical in the a position or a derivative thereof. Derivatives of α-hydroxy acid, as defined herein, are salts and/or lactides of an α-hydroxy acid.

Another subject of the invention is the use in cosmetics of the above compositions for the cleaning or care of the hair and/or of the scalp.

Other characteristics, aspects, and advantages of the invention will emerge more clearly on reading the description which will follow and the concrete, but in no way limiting, examples intended to illustrate it.

The nature of the anionic surfactant entering into the detergent compositions according to the invention is not critical. Thus, the anionic surfactants which may be used, alone or as mixtures, in the context of the present invention, include, but are not limited to, the salts (in particular the alkali metal salts, especially of sodium, ammonium salts, amine salts, amino alcohol salts or magnesium salts) of the following compounds: alkyl sulphates, alkyl ether sulphates, alkylamidoether sulphates, alkylarylpolyether sulphates and monoglyceride sulphates; alkyl sulphonates, alkyl phosphates, alkyl amide sulphonates, alkyl arylsulphonates, α-olefin sulphonates and paraffin sulphonates; alkyl sulphosuccinates, alkyl ether sulphosuccinates and alkyl amide sulphosuccinates; alkyl sulphosuccinamates; alkyl sulphoacetates; alkyl ether phosphates; acyl sarcocinates and N-acyltaurates, the alkyl or acyl radical of all these various compounds preferably containing from 12 to 20 carbon atoms. Among the anionic surfactants which may also be used, there may equally be mentioned fatty acid salts such as the salts of oleic acid, ricinoleic acid, palmitic acid and stearic acid, the acids of copra oil or of hydrogenated copra oil; acyl lactates in which the acyl radical contains 8 to 20 carbon atoms. It is also possible to use weakly anionic surfactants, such as the alkyl D-galactoside uronic acids and their salts, as well as polyoxyalkylenated carboxyl ethers, in particular those containing from 2 to 24 ethylene oxide groups, and their mixtures.

The nonionic surface-active agents are, themselves also, compounds which are well known per se. See in particular in this regard, "Handbook of Surfactants" by M. R. Porter, Blackie & Son editions (Glasgow and London), 1991, pp. 116–178, the disclosure of which is hereby incorporated by reference. The nature of these nonionic surface-active agents does not, in the context of the present invention, assume any critical character. Thus, they may in particular be chosen from polyethoxylated, polypropoxylated or polyglycerolated fatty alcohols, fatty alpha-diols, fatty alkylphenols or fatty acids having a fatty chain containing, for example 8 to 18 carbon atoms, the number of ethylene oxide or propylene oxide groups possibly ranging in particular from 2 to 50 and the number of glycerol groups possibly ranging in particular from 2 to 30. There may also be mentioned the copolymers of propylene and ethylene oxide, the condensates of propylene and ethylene oxide with fatty alcohols; polyethoxylated fatty amides preferably having from 2 to 30 moles of ethylene oxide, polyglycerolated fatty amides containing on average 1 to 5 glycerol groups and preferably 1.5 to 4; polyethoxylated fatty amines preferably having 2 to 30 moles of ethylene oxide; oxyethylenated fatty acid esters of sorbitan having 2 to 30 moles of ethylene oxide; fatty acid esters of sucrose, fatty acid esters of polyethylene glycol, alkylpolyglycosides, N-alkylglucamine derivatives, amine oxides such as ($C_{10}$–$C_{14}$) alkylamine oxides or N-acylaminopropylmorpholine oxides. It will be noted that the alkylpolyglycosides constitute nonionic surfactants which fall particularly well into the scope of the present invention.

The conditioning agents which may be used in the context of the present invention may be chosen from all those already known per se as enhancing the cosmetic properties of hair treated with detergent compositions, in particular cationic polymers, such as those described, for example, in European Patent Application EP-A-0,337,354 and in French Patent Applications FR-A-2,270,846, FR-A-2,383,660, FR-A-2,598,611, FR-A-2,470,596 and FR-A-2,519,863, the entire disclosures of which are hereby incorporated by reference; amphoteric polymers such as those described, for example, in European Patent Application EP-A-0,269,243, U.S. Pat. No. 3,836,537, the entire disclosures of which are hereby incorporated by reference, and the last two French Patent Applications cited above; silicones and their derivatives, such as those described, for example, in European Patent Applications EP-A-0,398,177 and EP-A-0,492,657, the entire disclosures of which are hereby incorporated by reference; and, although to a far lesser extent, certain anionic polymers.

The detergent compositions in accordance with the invention may obviously contain one or more anionic surface-active agents, one or more nonionic surface-active agents and one or more conditioning agents.

According to an essential characteristic of the detergent hair compositions according to the invention, these compositions contain at least one carboxylic acid which is hydroxylated in the a position (which compound is also referred to as an α-(alpha) hydroxy acid) or a derivative thereof. Acid derivatives, as defined herein, are associated salts (salts with organic bases or alkali metal, for example) or lactides (obtained, for example, by autoesterification of α-hydroxy acid molecules).

This α-hydroxy acid may obviously consist of a mono- or polycarboxylic acid containing one or more hydroxyl functions, at least one of these hydroxyl functions necessarily occupying a position α to the said acid (carbon adjacent to a carboxylic function). This acid may be present in the final detergent composition in free acid form and/or in the form of one of its combined salts, e.g., salts with an organic base or with an alkali metal in particular, depending in particular on the final pH imposed on the composition, or alternatively possibly in the form of the corresponding lactide (obtained, for example, by autoesterification of the molecules). Preferably, the α-hydroxy acid is selected from linear α-hydroxy acids with less than 5 carbon atoms and aromatic α-hydroxy acids. The detergent compositions in accordance with the invention may, of course, contain one or more α-hydroxy acids.

By way of examples of such compounds there may be mentioned, among others, citric acid, lactic acid, methyllactic acid, phenyllactic acid, malic acid, mandelic acid, glycolic acid, tartronic acid, tartaric acid, gluconic acid, benzylic acid and 2-hydroxycaprylic acid. Other compounds of α-hydroxy acid type suitable for the present invention are those cited in Patent Application EP-A-0,413,528, the disclosure of which, in this regard, is hereby incorporated by reference in its entirety.

The acids which are cosmetically compatible with and acceptable for the hair, the skin and/or the scalp will preferably be chosen. According to a particularly preferred embodiment of the present invention, the α-hydroxy acid used is chosen from citric acid lactic acid and tartaric acid.

According to another important characteristic of the detergent compositions according to the invention, the α-hydroxy acid or acids are present in these compositions in amounts of at least 2% by weight, preferably at least 3% by weight relative to the whole of the composition. More preferably, the α-hydroxy acid content ranges from 2 to 10% by weight and even more preferably from 4 to 5% by weight. It will be noted that these concentrations are markedly higher than those which are sometimes encountered in shampoos of the prior art when certain acids have been employed solely for the purposes of adjusting the pH.

As a guide, the detergent formulations in accordance with the invention generally have the following compositions:
(i) anionic surfactant(s): from 5 to 50% by weight, preferably from 5 to 20% by weight, relative to the total weight of the detergent formulation;
(ii) nonionic surfactant(s): from 5 to 30% by weight and preferably from 5 to 20% by weight relative to the total weight of the detergent formulation;
(iii) conditioning agent(s): from 0.01 to 10% relative to the total weight of the detergent formulation:
(iv) α-hydroxy acid(s): as indicated above.

The vehicle or support, defined herein as a cosmetically acceptable medium, for the detergent compositions according to the invention is preferably an aqueous medium such as water, or an aqueous-alcoholic solution of a lower alcohol such as ethanol, isopropanol or butanol.

The detergent compositions according to the invention have a final pH which generally ranges from 2 to 8. Preferably, this pH ranges from 3 to 7. Adjustment of the pH to the desired value may be carried out conventionally by addition of a base (organic or inorganic) to the composition, for example of aqueous ammonia or a primary, secondary or tertiary (poly)amine such as monoethanolamine, diethanolamine, triethanolamine, isopropanolamine or 1,3-propanediamine. Aqueous ammonia is preferably used. Neutralization of the α-hydroxy acid by a base has the supplementary advantage of favoring formation of a buffer which, by avoiding fluctuations in pH, enables the stability of the shampoo to be enhanced; moreover, this neutralization generally causes a spontaneous thickening of the shampoo, which is often sought in this type of application.

The detergent compositions according to the invention may, of course, additionally contain all the usual adjuvants encountered in the field of shampoos, for example such as fragrances, preserving agents, sequestering agents, thickening agents, softening agents, foam modifiers, dyes, pearling agents, moisturizing agents, anti-dandruff or anti-seborrhoeia agents, vitamins, sunscreen agents and others.

These compositions may be provided in the form of liquids which are thickened to a greater or lesser extent, creams or gels, and they are mainly suitable for the washing, the care and/or the beauty of the hair.

Concrete examples illustrating the invention will now be given. It is to be understood that these examples are merely illustrative and not limiting.

EXAMPLE

Three shampoos in accordance with the invention (A, B and C), which had the following compositions, were prepared and tested:
Shampoo A:
Sodium lauryl ether sulphate and magnesium lauryl ether sulphate containing 4 mol of ethylene oxide, sold under the name TEXAPON ASV by HENKEL (anionic surfactant) 6.5 g Glucoside caprilyl-capryl ether, sold under the name ORA-MIX CG 110 by SEPPIC (nonionic surfactant) 15 g
Vinylpyrrolidone/dimethyl aminoethyl methacrylate copolymer quaternized with diethyl sulphate, sold under the name GAFQUAT 755 by the company ISP (conditioning agent) 0.2 g
EDTA 0.25 g
Preserving agents 0.31 g
Citric acid 5 g
Water qs 100 g The pH of this shampoo was adjusted to pH 5 by addition of aqueous ammonia.

Shampoo B:
Sodium lauryl ether sulphate containing 2.2 mol of ethylene oxide (anionic surfactant) 5.6 g
Polyglycerolated dodecanediol containing 3.5 mol of glycerol, prepared according to FR-A-2 091 516, the disclosure of which is hereby incorporated by reference (nonionic surfactant) 10 g
Cross-linked and quaternized hydroxyethyl cellulose, sold under the name JR 400 by the company UNION CARBIDE (conditioning agent) 0.2 g
Oxyethylenated tallow (60 mol of ethylene oxide) myristyl glycol ether, sold under the name ELFACOS GT 282 S by AKZO (thickening agent) 1.5 g
EDTA 0.25 g
Preserving agents 0.31 g
Citric acid 5 g
Water qs 100 g The pH of this shampoo was adjusted to pH 5 by addition of aqueous ammonia.

Shampoo C:
Sodium lauryl ether sulphate containing 2.2 mol of ethylene oxide (anionic surfactant) 4.2 g
Oxyethylenated lauric alcohol containing 12 mol of ethylene oxide, sold under the name LAUROPAL 12 by WITCO (nonionic surfactant) 7 g
Vinylpyrrolidone/dimethylaminoethyl methacrylate copolymer quaternized with diethyl sulphate, sold under the name GAFQUAT 755 by the company ISP (conditioning agent) 0.2 g
Copra acid diethanolamide (thickening agent) 3 g
EDTA 0.25 g
Preserving agents 0.31 g
Citric acid 5 g
Water qs 100 g The pH of this shampoo was adjusted to pH 5 by addition of aqueous ammonia.

The cosmetic performance of the above shampoos was assessed by a panel of experts using sensory analysis tests conducted in vivo on sensitized human hair (in this case, permanent-waved hair). The procedure was as follows: the shampoos were applied to wet hair, then emulsified and finally rinsed with water after being left on the hair for a few minutes; after drying, the hair was examined by the experts.

As a comparison, three compositions A', B' and C' identical respectively to the compositions A, B and C above were also tested, according to the same procedure, the only difference being that this time all three lacked α-hydroxy acids and that they were brought to the same pH as that of the corresponding compositions of the invention by addition of hydrochloric acid.

The panel of experts judged and concluded that the compositions A, B and C in accordance with the invention had, relative to the corresponding comparative compositions, the following representative beneficial effects: provision of lightness, suppleness, smoothness and shine to dry hair.

Moreover, mechanical strength tests conducted on hair which had been repeatedly treated several tens of times with the comparative shampoos, on the one hand, and the shampoos in accordance with the invention, on the other hand, showed that, in this latter case, there was no appreciable loss of mechanical strength of the hair.

What is claimed is:

1. A detergent hair composition comprising a cosmetically acceptable medium containing:
    (a) at least one anionic surface-active agent;
    (b) at least one nonionic surface-active agent;
    (c) at least one conditioning agent selected from cationic polymers, amphoteric polymers, silicones, and anionic polymers; and
    (d) from at least 2% to less than 10% by weight relative to the total weight of the detergent hair composition of at least one ingredient selected from citric acid, lactic acid, tartaric acid, and salts of said acids.

2. A composition according to claim 1, wherein said at least one ingredient is present in an amount of at least 3% by weight.

3. A composition according to claim 1, wherein the at least one anionic surface-active agent is present in an amount of from 5 to 50% by weight relative to the total weight of the composition.

4. A composition according to claim 3, wherein the at least one anionic surface-active agent is present in an amount of from 5 to 20% by weight relative to the total weight of the composition.

5. A composition according to claim 1, wherein the at least one nonionic surface-active agents is present in an amount of from 5 to 30% by weight relative to the total weight of the composition.

6. A composition according to claim 5, wherein the at least one nonionic surface-active agent is present in an amount of from 5 to 20% by weight relative to the total weight of the composition.

7. A composition according to claim 1, wherein the at least one conditioning agent is present in an amount of from 0.01 to 10% by weight relative to the total weight of the composition.

8. A composition according to claim 1, wherein said composition is an aqueous or aqueous-alcoholic composition.

9. A composition according to claim 1, wherein said composition has a pH ranging from 2 to 8.

10. A composition according to claim 9, wherein said pH ranges from 3 to 7.

11. A method for the cleaning or care of the hair or the scalp comprising the step of applying to the hair or scalp a cosmetically effective amount of a composition as defined in claim 1.

12. A method according to claim 11, wherein said hair is sensitized hair.

13. A composition according to claim 1, wherein said at least one ingredient is present in an amount ranging from 4–5% by weight, relative to the total weight of said detergent hair composition.

* * * * *

UNITED STATES PATENT AND TRADEMARK OFFICE
CERTIFICATE OF CORRECTION

PATENT NO.: 6,051,213

DATED: April 18, 2000

INVENTOR(S): Bernard BEAUQUEY, Daniele CAUWET, Sandrine DECOSTER and Claude DUBIEF It is certified that an error appears in the above-identified patent and that said Letters Patent is hereby corrected as shown below:

Claim 5, col. 6, line 35, change "agents" to --agent--.

Signed and Sealed this

Thirtieth Day of January, 2001

*Attest:*

Q. TODD DICKINSON

*Attesting Officer*  *Director of Patents and Trademarks*